(12) United States Patent
Morris et al.

(10) Patent No.: US 6,702,742 B1
(45) Date of Patent: Mar. 9, 2004

(54) METHOD FOR RAPID STABILIZATION OF QUANTITATIVE ULTRASONIC MEASUREMENTS

(75) Inventors: Richard Franklin Morris, Stoughton, WI (US); Wynn K. Wacker, Madison, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/065,110

(22) Filed: Sep. 18, 2002

(51) Int. Cl.[7] .................................................. A61B 8/00
(52) U.S. Cl. ...................................... 600/437; 600/449
(58) Field of Search ................................. 600/437, 438, 600/449; 73/597, 599

(56) References Cited

U.S. PATENT DOCUMENTS

| | | | | |
|---|---|---|---|---|
| 4,424,814 A | * | 1/1984 | Secunda | 600/454 |
| 4,427,115 A | * | 1/1984 | Laipply | 206/484 |
| 6,027,449 A | * | 2/2000 | Mazess et al. | 600/449 |
| 2002/0068871 A1 | * | 6/2002 | Mendlein et al. | 600/459 |

\* cited by examiner

Primary Examiner—Francis J. Jaworski
(74) Attorney, Agent, or Firm—Quarles & Brady LLP; Carl Horton

(57) ABSTRACT

Alcohol is used as a coupling medium between an ultrasonic transducer and patient skin providing rapid settling of quantitative measurements.

16 Claims, 1 Drawing Sheet

METHOD FOR RAPID STABILIZATION OF QUANTITATIVE ULTRASONIC MEASUREMENTS

BACKGROUND OF INVENTION

The present invention relates to medical ultrasound imaging equipment and, in particular, to a biocompatible material for coupling ultrasonic energy between a patient's skin and an ultrasonic transducer used in such equipment.

Ultrasound may be used to measure the physical characteristics of living tissue. In echo ultrasound, an ultrasonic transducer is placed against the skin to transmit sound into the patient, and then to receive echo signals caused by the reflections of the ultrasonic energy across interfaces between materials of different acoustical properties. In transmission ultrasound, an ultrasonic transmitting transducer is placed against the skin on one side of the patient to transmit sound through the patient to be received by a second ultrasonic transducer placed against the skin on the other side of the patient.

Transmission ultrasound finds considerable use in quantitative measurements of tissue characteristics and, in particular, in the field of bone densitometry where measurements of speed of sound and broadband ultrasonic attenuation (BUA) may be used to characterize bone health. Such systems are described in U.S. Pat. Nos. 4,930,511, 5,042,489, 5,054,490, 5,099,849, 5,119,820, 5,218,963, 5,343,863, 5,349,959, 5,483,965, 5,603,325, 5,840,029, 6,027,449, 6,277,076, and 6,364,837, all assigned to the assignee of the present invention and hereby incorporated by reference.

The delivery of ultrasound into the patient requires an efficient coupling path between the transducer and the patient's skin usually facilitated by a coupling material. Such coupling materials are typically selected to be hypoallergenic, slow to dry, and of comparable acoustic qualities to water (the principal constituent of tissue). Some commonly used coupling materials are glycerol, water, and oils.

In many applications, a gel material is used because of its lessened tendency to flow from the region in which it is applied and its ability to fill gaps between the ultrasonic transducer and the skin. U.S. Pat. No. 4,002,221 describes a gel coupling agent having a viscosity similar to mayonnaise and formed from copolymers of methylvinyl-ether and maleic acid and carboxy-polymethylene polymer with alkali metal salts as thickeners. U.S. Pat. No. 4,459,854 describes a coupling material composed of a hydrogel being a copolymer of vinyl pyrrolidone and phenolethyl methacrylate. Numerous of ultrasound coupling gels are commercially available.

Precise quantitative measurements in bone densitometry studies often require a stabilization period after the coupling material has been applied to the patient and the ultrasonic transducers have been positioned. This stabilization period is about one minute with maximum stabilization occurring as much as fifteen to twenty minutes later. The mechanism underlying this need for a stabilizing period is not well understood.

SUMMARY OF INVENTION

The present inventor has determined that the stabilization period needed for quantitative bone density measurements is essentially eliminated (approximately fifteen seconds) when a thin coating of alcohol is used as the coupling material between the ultrasonic transducer and skin.

While the inventor does not wish to be bound by a particular theory, it is believed that the reduction of stabilization time may result from alcohol's ability to penetrate or wet the skin very quickly, which in turn may be a function of its extremely low surface tension. In contrast, gels, for example, may tend to entrap air and impede the wetting of the skin's surface.

Unlike gels and other coupling materials, the high volatility of the alcohol makes for easy cleanup and does not leave a residue on the patient's skin. Alcohol has a sterilizing property, presents a low safety hazard, is easily dispensed from a spray bottle without danger of contamination, and is readily available in the hospital or clinic environment.

The invention may be particularly suitable for ultrasound systems that use an inflated bladder having a convex outer surface where little gap filling is required and where the contact area of the bladder during inflation spreads outward clearing bubbles from the region.

These particular objects and advantages may apply to only some embodiments falling within the claims and thus do not define the scope of the invention.

DETAILED DESCRIPTION

Figure 1:
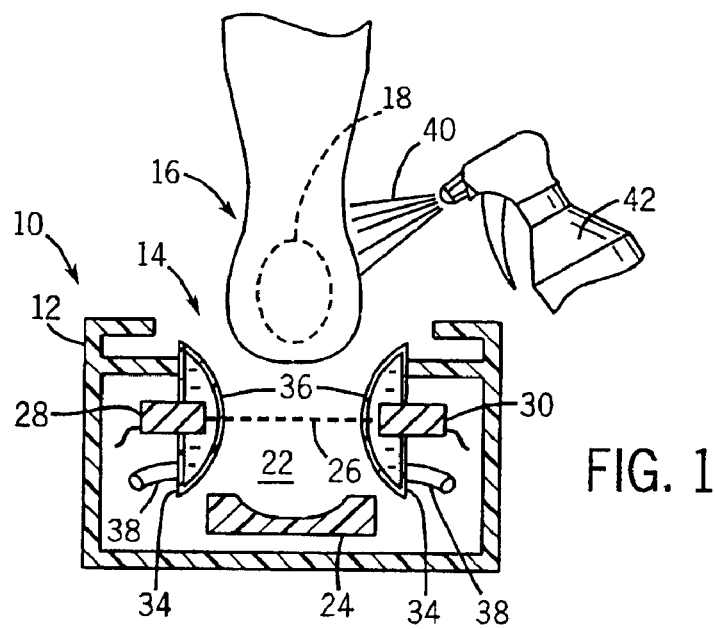
FIG. 1 is a cross-sectional view through a transmission ultrasound machine intended for measurement of the os calcis bone of the heel, showing opposed transducers with deflated coupling bladders spaced apart to receive the heel therebetween, and showing application of an alcohol spray to skin surfaces.
Figure 2:
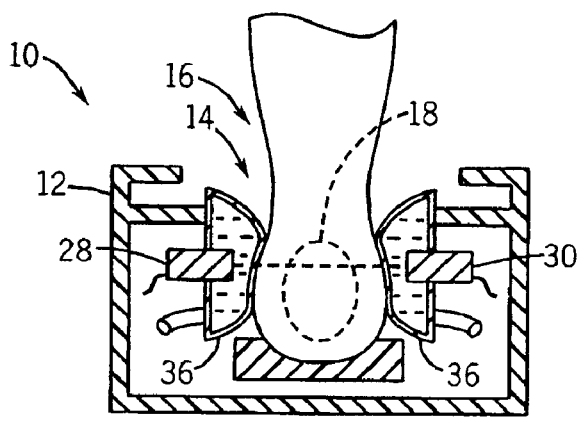
FIG. 2 is a figure similar to that of FIG. 1 showing the heel in place between the bladders with the bladders inflated to provide coupling of ultrasonic energy from the transducers to the skin through an alcohol layer.

Referring now to FIGS. 1 and 2, a bone densitometer 10 providing for ultrasonic measurement of bone health includes a housing 12 having an opening 14 in the upper surface sized to receive a patient's heel 16.

The opening 14 reveals a chamber 22 sized to receive the patient's heel 16 on a guide plate 24 so that the os calcis 18 is positioned along an axis 26 between a first transmitting transducer 28 and a second receiving transducer 30 flanking the heel 16. The transducers 28 and 30 each extend through a circular backer plate 34 covered with a flexible silicon membrane 36 attached around its circumference to the circumference of the backer plate so as to define an enclosed volume covering the faces of transducers 28 and 30 exposed to the chamber 22. A liquid, typically a water and alcohol mixture, is introduced through passageways 38 communicating with the enclosed volume to inflate the membrane 36 expanding it outward to engage the skin of the patient's heel 16 when the patient's heel 16 is positioned within the housing 12.

As will be understood from this description, the membranes 36 are outwardly convex to initially contact the foot at a limited area that expands outward with inflation to squeeze out air.

During operation of the bone densitometer 10, a series of ultrasound pulses may be produced by the transducer 28 driven by appropriate circuitry to pass along axis 26 through the os calcis 18 to receiving transducer 30. The ultrasound pulses received by the transducer 30 are then analyzed to deduce the speed of sound (SOS) through the patient's heel 16 (being principally that through the os calcis 18) and a broadband attenuation (BUA) as is well understood to those of ordinary skill in the art.

Referring now to FIG. 1, before insertion of the heel 16, an alcohol spray 40 may be applied to both the left and right side of the heel 16 in the region where they will contact the membranes 36 upon inflation of the membranes 36. The alcohol spray 40 is preferably isopropyl alcohol in 70 to 90% concentration of alcohol as may be practically obtained and stored. The alcohol spray 40 is not mixed with other thickeners to maintain a low viscosity. Trace amounts of additional material may be added to the alcohol spray 40 including surfactants, perfumes, colorings, and the like.

The viscosity of the alcohol spray 40 is preferably comparable to the viscosity of water at room temperature (approximately one centi-Poise (cP)) and typically no greater than ten centi-Poise. The surface tension of the alcohol spray 40 will be comparable to the surface tension of isopropyl alcohol (twenty-two dynes per centimeter) but in any event will be less than the surface tension of water at room temperature of 72.8 dynes per centimeter.

The amount of alcohol spray 40 applied is such as to coat the heel 16 sufficiently so that alcohol just begins to run down the vertical sides of the skin. The alcohol spray 40 may be applied with a conventional spray bottle 42 which need not contact the patient eliminating contamination problems.

Alternatively, the alcohol may be applied to the membranes 36 before insertion of the heel 16. In yet another alternative, the alcohol spray 40 may be applied to either of the heel 16 or membranes 36 with the membranes 36 pre-inflated and the heel 16 is slid between them. The alcohol need not be applied in a spray but may be painted on or the like with other forms of applicators such as a brush.

Referring to FIG. 2, the volatile alcohol spray 40 is immediately covered by the membranes 36 (as seen in FIG. 2) that serve to retard additional evaporation prior to the measurement.

Figure 3:
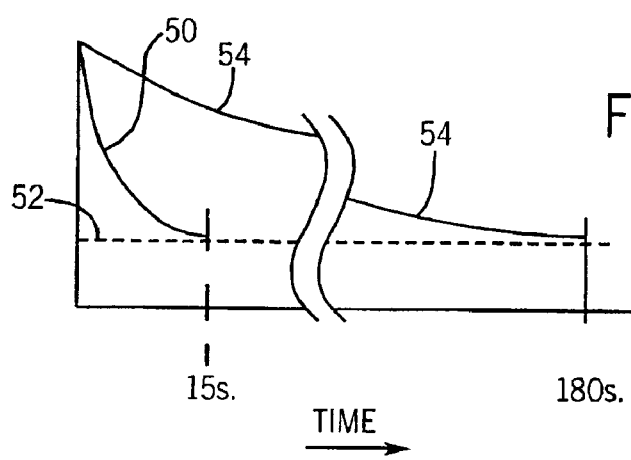
FIG. 3 is a chart showing change in measured bone density values over time obtained with the alcohol spray versus a conventional gel coupling material.

Referring now to FIG. 3, using the alcohol spray 40 as a coupling material provides measured ultrasonic parameters (e.g., speed of sound, broadband ultrasonic attenuation) that stabilize as generally indicated by plot line 50 approaching an asymptote 52 within approximately fifteen seconds. In contrast, use of a conventional gel provides measured ultrasonic parameters that stabilize as generally indicated by plot line 54 in as much as 120 to 180 seconds.

When the heel 16 is removed from the bone densitometer 10, the alcohol spray 40 which has not been absorbed into the skin, quickly evaporates, avoiding the need to clean gel off of the patient's foot such as might soil hosiery.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A method of coupling an ultrasonic transducer to skin comprising the steps of:

applying a coating of alcohol unmixed with thickener to the skin in a contact area free from a gel coupling material; and immediately compressing a flexible coupler between the coated contact area and the ultrasonic transducer to trap a liquid film of unabsorbed alcohol at the skin.

2. The method of claim 1 wherein the coating of alcohol is applied directly to skin in the contact area.

3. The method of claim 1 wherein the coating of alcohol is applied to a surface of the flexible coupling and applied indirectly to the skin when the flexible coupler is compressed against the skin.

4. The method of claim 1 including the step of mixing the alcohol with water within a ratio of 70–90% alcohol before applying the alcohol to the skin.

5. The method of claim 1 including the step of selecting isopropyl alcohol as the alcohol.

6. The method of claim 1 including the step of mixing the alcohol with other materials such that the viscosity of the liquid film is less than 2 cP.

7. The method of claim 1 wherein the alcohol is applied by spray.

8. The method of claim 1 further including the step of orienting the interface between the flexible coupler and the skin so that the interface between the flexible coupler and the skin is substantially vertical.

9. The method of claim 1 wherein the flexible coupler is a fluid filled membrane and including the step of deforming the flexible coupler against the skin during the compression.

10. The method of claim 9 wherein the membrane is a silicone membrane and including the step of directly contacting the silicone membrane to the liquid film.

11. The method of claim 1 wherein the transducer operates as an ultrasonic receiver and including the step of transmitting ultrasound from the transducer into the skin.

12. The method of claim 1 wherein the transducer operates as an ultrasonic receiver, and including the step of receiving ultrasound from the skin into the transducer.

13. The method of claim 1 wherein the contact area consists of a first and second contact area on opposite sides of a patient member and including the step of compressing the flexible coupler between the first contact area and the ultrasonic transducer and compressing a second flexible coupler between the second contact area and a second ultrasonic transducer.

14. The method of claim 13 including the step of measuring ultrasonic energy passing through the patient member to produce an indication of at least one of: speed of sound and broadband ultrasonic attenuation.

15. The method of claim 1 wherein the step of applying the coating applies the coating in a thickness causing flow of the alcohol on a vertical skin surface.

16. The method of claim 1 wherein the flexible coupler is elastically convex at the interface between the flexible coupler and the contact area and wherein the step of compressing the flexible coupler against the skin expands the coupler outward from an initial contact area.

\* \* \* \* \*